(12) United States Patent
Askari

(10) Patent No.: US 6,171,855 B1
(45) Date of Patent: Jan. 9, 2001

(54) VECTORS

(75) Inventor: Frederick K. Askari, Ann Arbor, MI (US)

(73) Assignee: The Regents of the University of Michigan, Ann Arbor, MI (US)

( * ) Notice: Under 35 U.S.C. 154(b), the term of this patent shall be extended for 0 days.

(21) Appl. No.: 09/085,848

(22) Filed: May 28, 1998

(51) Int. Cl.$^7$ .............................. C07H 21/04; C12N 5/00; C12N 15/63; C12P 21/04

(52) U.S. Cl. ..................... 435/320.1; 435/70.1; 435/325; 435/455; 536/24.1

(58) Field of Search ................................. 435/320.1, 455, 435/325, 235.1; 514/44; 536/24.1

(56) References Cited

U.S. PATENT DOCUMENTS

| | | |
|---|---|---|
| 5,166,320 | 11/1992 | Wu et al. .............................. 530/395 |
| 5,354,844 | 10/1994 | Beug et al. ........................... 530/345 |
| 5,585,362 | 12/1996 | Wilson et al. .......................... 514/44 |

OTHER PUBLICATIONS

Benvenisty and Reshef, "Direct introduction of genes into rats and expression of the genes," *Proc. Nat. Acad. Sci. USA*, 83:9551–55 (1986).

Doty et al., "Strand Separation and Specific Recombination in Deoxyribonucleic Acids: Physical Chemical Studies," *Proc. Natl. Acad. Sci. USA* 46:461–476 (1960).

Dubensky et al., "Direct transfection of viral and plasmid DNA into the liver or spleen of mice," *Proc. Nat. Acad. Sci. USA* 81:7529–33 (1984).

Gaynor and Berk, "Cis–Acting Induction of Adenovirus Transcription," *Cell* 33:683–693 (1983).

Graham et al., "Characteristics of a Human Cell Line Transformed by DNA from Human Adenovirus Type 5," *J. Gen. Virol.* 36:59–72 (1977).

Imperiale et al.; "Common Control of the Heat Shock Gene and Early Adenovirus Genes: Evidence for a Cellular E1A–like Activity," *Mol. Cell Biol.* 4:867–874 (1984).

Maniatis, T. et al., "Regulation of Inducible and Tissue–Specific Gene Expression," *Science* 236:1237–1244 (1987).

Marmur and Lane, "Strand Separation and Specific Recombination in Deoxyribonucleic Acids Biological Studies," *Proc. Natl. Acad. Sci. USA* 46:453–461 (1960).

Nevins, "Mechanism of Activation of Early Viral Transcription by the Adenovirus E1A Gene Product," *Cell* 26:213–220 (1981).

Qin et al., "Promoter Attention in Gene Therapy: Interferon–γ and Tumor Necrosis Factor–α Inhibit Transgene Expression," *Human Gene Therapy* 8:2019–2029 (1997).

Wagner, et al., "Transferrin–polycation–DNA complexes: The effect of polycations on the structure of the complex and DNA delivery to cells," *Proc. Natl. Acad. Sci.*, 88:4255–4259 (1991).

Wolff et al., "Direct Gene Transfer into Mouse Muscle in Vivo," *Science*, 247:1465–68 (1990).

Yang et al., "Cellular immunity to viral antigens limits E1–deleted adenoviruses for gene therapy," *Proc. Natl. Acad. Sci. USA* 91:4407–4411 (1994).

Yang and Wilson, "Clearance of Adenovirus–Infected Hepatocytes by MHC Class I–Restricted CD4+ CTLs In Vivo," *J. Immunol.* 155:2564–2570 (1995).

F. Askari et al., "Complete correction of hyperbilirubinemia in the Gunn rat model of Crigler–Najjar syndrome type I following transient in vivo adenovirus–mediated expression of human bilirubin UDP–glucuronosyltransferase," Gene Therapy, 3, 381–388 (1996).

S.P. Bell et al., "Assembly of alternative multiprotein complexes directs rRNA promoter selectivity," *Genes & Development*, 943–954 (1990).

J.A. Skinner et al., "In vivo mutagenesis and transcriptional analysis of a mouse ribosomal promoter element," *Proc. Natl. Acad. Sci. USA*, 81(7):2137–41 (1984).

J.K. Ritter et al., "Cloning of Two Human Liver Bilirubin UDP–glucuronosyl–transferase cDNAs with Expression in COS–1 Cells," *J. Biol. Chem.*, 288(2):1043–1047 (1991).

Florence Paillard, "Promoter Attenuation in the Gene and Remedies: Causes and Remedies," *Hum. Gene Ther.*, 8(17): 2009–10 (Nov., 1997).

C.S. Pikaard, "Ribosomal gene domains can function as artificial enhances of RNA polymerase I transcription, supporting a promoter origin for natural enhancers in *Xenopus*," *Proc. Natl. Acad. Sci. USA*, 91:464–468 (1994).

C.A. Radebaugh et al., "Identification of Previously Unrecognized Common Elements in Eukaryotic Promoters," *J. Biological Chem.*, 272(6):3141–3144 (1997).

J.F. Engelhardt et al., "Ablation of E2A in recombination adenovirus improves transgene persistence and decreases inflammatory response in mouse liver," *Proc. Natl. Acad. Sci. USA*, 91:6196–6200 (1994).

M. Marilley and P. Pasero, "Common DNA structural features exhibited by eukaryotic ribosomal gene promoters," *Nuc. Acids Research*, 24(12):2204–2211 (1996).

R.R. Genuario et al., "Comparative utilization of transcription factor GABP by the promoters of ribosomal protein genes rpL30 and rpL32," *Gene Expression*, 3(3):279–288 (1993) Abstract.

X. Ling and N. Arnheim, "Cloning and identification of the pig ribosomal gene promoter" Gene, 150(2):375–379 (1994).

Friedmann, T. Overcoming the obstacles to gene therapy. Sci. Am. Jun. 1997 pp. 96–101.*

Marshall, E. Gene therapy's growing pains. Science 269: 1050–1055, Aug. 1995.*

(List continued on next page.)

*Primary Examiner*—Karen M. Hauda
*Assistant Examiner*—Anne-Marie Baker
(74) *Attorney, Agent, or Firm*—Medlen & Carroll, LLP

(57) ABSTRACT

The present invention provides improved vectors, including viral vectors such as adenovirus vectors. The vectors comprise ribosomal promoters in operable combination with a gene of interest. The improved vectors are useful for a wide variety of gene therapy applications.

11 Claims, 11 Drawing Sheets

OTHER PUBLICATIONS

Orkin and Motulsky Report and recommendations of the panel to assess the NIH investment in research on gene therapy, Dec. 1995.*

Verma et al. Gene therapy—promises, problems, and prospects. Nature 389: 239–242, Sep. 1997.*

Miesfeld et al. Identification of the in vivo and in vitro origin of transcription in human rDNA. Nucl. Acids Res. 10(13): 3933–3949, 1982.*

Dudov and Perry The gene family encoding the mouse ribosomal protein L32 contains a uniquely expressed intron-containing gene and an unmutated processed gene. Cell 37: 457–468, Jun. 1984.*

Stratford–Perricaudet et al. Evaluation of the transfer and expression in mice of an enzyme encoding gene using a human adenovirus vector. Human Gene Therapy 1:241–256, 1990.*

Lavenu et al. The cis–acting elements known to regulate c–myc expression ex vivo are not sufficient for correct transcription in vivo. Oncogene 9: 527–536, 1994.*

Zahradka et al. Characterization of a mammalian ribosomal protein gene promoter. Biochem. Cell Biol. 68: 949–956, 1990.*

* cited by examiner

GAGTCTCTGTTTGCTACCTCCCAGCCTCAAGGAGGCACCCTCGGGAACCAACAATTTAAAAAGCTATTGGGCTTCCACTTAGGGCGGAAATAAATGCCCC
       -350                    -300                    -250                    -200                    -150
ACCTAGCAGGTCTTAGCTCAAAAAAAACAAAAATCTTAGTAGTCCCAAGAGAAAATAAATTTAGTTCACTCTAAGATGTTAATGTCTACTACAGAACACTAGTCCAC
              -250                    -200                    -150                    -100                    -50
TAGGGTTTTTTTCAGTATCATTTCTCAGGCACACATCTTAGTTTTCTTTAGAGGACCCAGAGCCGGAAGTGCTTCCCTTTTCTCTGTCTAGGACCTAAGACTCCGTCCATCATACCTTGCGC
                                        5' - EXON 1        INTRON 1                                              100
GCCCGGCCGCCCTCTTC CTTCTCCTCGGGCCTGCCTACGAGGTGCTGCTGCAC GTGAGTCTGTATCGGCGGCATCCGCGCCCGGCTTCGACGGGACCCCGTCTC
                    1                                
CGGGTGGGGAGGCCTCGGCGGCGGCGGGGCCGCCTCCGCACCAGCGTGGTAGTGGCGGCGCACCCCGCCGAGAGTTTCGGAGCGGCAAGCCCGGCGGGAGACGGGCCTGCCGCTCGCCAGTGAGC
                    150                    200                    250                                        450
GCCATGCGGCCCGAGAGTTTCGGAGCGGCAAGCCCGGCGGGAGACGGGCCTGCCGCTCGCCAGTGAGC
AGAAATGCTTTCCGAAGGCAAGCCCGGCGGGAGACGGGCTGCGAGACGGACGAGGAGGACAGACGGAGCGGACTGGTGGCGTGTT
                    350                    400                    450
AGGAGTGCATGGTGGCTTTGCGTATTTAAGGGGCAACACTTCAAACATAACGAAGCTTAGTGGACCGGATTGCCGCCCTCGCCACCAGAGACCTGCTGGGGTTCTGTAAGATCG
                    550                                                                                  700
GTTGCGGTTCTTTGAGGTTCGGAGTGGTGAGTGAGATGAACCACTGACCTCTTGGGATCGCGTCTCGGAGAGTAGCTAGTATTCTTCGAGCTTCGGAAGCAAGAGGGAGAGCAAGCCTAGCAGA
                    650                                        750                                        800
GGTACCCCATTTCATTTCCAGTTTGCTCGGTAGCTCGGTGATTGGAAGACACTCTGCAACATTACTCACTGAAGGCCTGAGACGCAGCCACCTCCCAGTTTCTTTACTAACTTGGGTCTG
EXON 2                                                                                                    900
ACTTTTTGTCAAAAAG GCATC ATG GCT GCC CTC CGG CCT CTG GTG AAG CCC AAG ATC GTC AAA AAG AGG ACC AAG AAG TTC ATC AGG CAC CAG TCA
                       Met Ala Ala Leu Arg Pro Leu Val Lys Pro Lys Ile Val Lys Lys Arg Thr Lys Lys Phe Ile Arg His Gln Ser

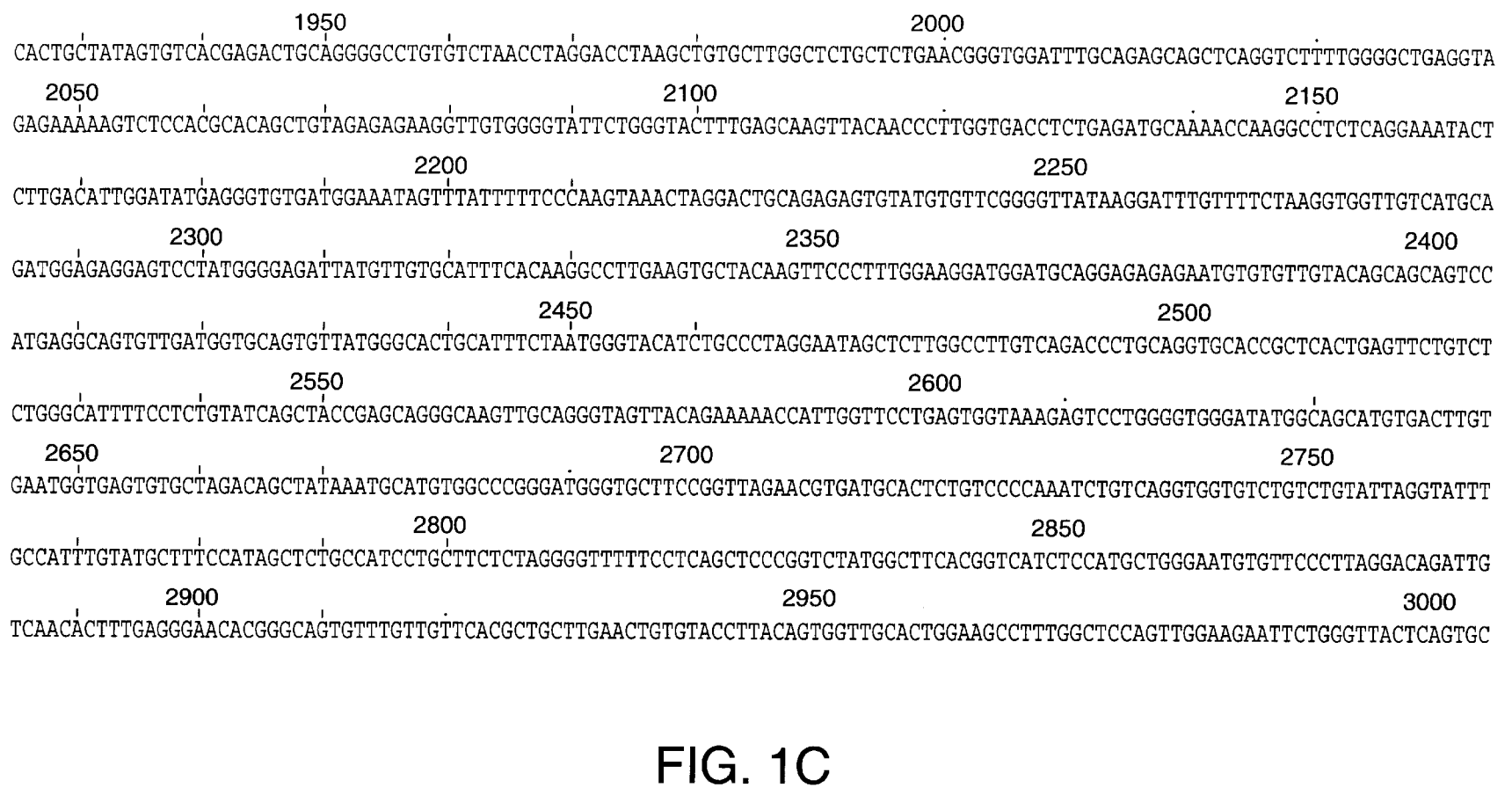

```
                                                                                                                         2000
CACTGCTCTATAGTGTCACGAGACTGCAGGGGCCCTGCTGTGTCTAACCTAGGACCTGTGCTCTTGGCTCTGCTCTGAACGGGTGATTTGCAGAGCAGTCAGTCTTTTGGGGCTGAGGTA
       2050                      2100                     2150
GAGAAAAGTCTCCACGCACAGCTGTAGAGAGAAGGTTGTGGGGTATTCTGGGTACTTTGAGCAAGTTACAACCCCTTGGTGACCTCTGAGATGCAAAACCAAGGCCTCTCAGGAAATACT
                      2200                     2250
CTTGACATTGGATATGAGGGTGTGATGGAAATAGTTTATTTTTCCCAAGTAAACTAGGACTGCAGAGAGTGTATGTGTTCGGGGTTATAAGGATTTGTTTCTAAGGTGGTTGTCATGCA
            2300                    2350                                                                                2400
GATGGAGAGGAGTCCTATGGGGAGATTATGTCGTCATTTCACAAGGCCCTTGAAGTGCTACAAGTTCCCTTTGAAGGATGCAGGAGGATGCAGGAGAGAATGTGTTGTACAGCAGTCC
                      2450                                             2500
ATGAGGCAGTGTTGATGGTGCAGTGTTATGGGCACTGCATTTCTAATGGGTACATCTGCCCTAGGAATAGCTCTTGGCCTTGTCAGACCCTGCAGGTGCACCCTCACTGAGTTCTGTCT
                       2550                    2600                                                                     2650
CTGGGCATTTCCCTCTGTATCAGCTACCGAGCAGGGCAAGTTGCAGGGTAGTTACAGAAAAACCATTGGTTCCTGAGTGGTAAAGAGTCCTGGGGTGGATATGGCAGCATGTGACTTGT
                       2700                                           2750
GAATGGTGAGTGTGCTAGACAGCTATAAATGCATGTGGCCCGGGATGGGGTGCTTCCGGTTAGAACGTGATGCACTCTGTCCCCAAATCTGTCAGGTGGTCTGTCTGTATTAGGTATTT
                       2800                    2850
GCCATTTGTATGCTTTCCATAGCTCTGCCATCCTGCCTGCTTCTCCTAGGGGTTTTTCCTCAGCTCCCGGTCTATGGCTTCACGGTCATCTCCATGCTGGGAATGTTCCCTAGGACAGATTG
                       2900                    2950                                          3000
TCAACACTTTGAGGGAACACGGGCAGTGTTTGTTGTTCACGCTGCTTGAACTGTGTACCTTACAGTGGTTGCACTGGAAGCCTTTGGCTCCAGTTGGAAGAATTCGGGTTACTCAGTGC
```

FIG. 1C

```
                                              3100
                    3050           EXON 4                      TCT TAC TGT GCT GAG ATT GCT CAC AAT GTG TCC TCT AAG AAC CGA AAA
GACGACGAATTAAGCGATTCCCTGGTGACCTTTCTGGTTTGCTTCTCTTTCAG↓A        S   Ser Tyr Cys Ala Glu Ile Ala His Asn Val Ser Ser Lys Asn Arg Lys
                                                         3150                                                                    3200
GCC ATT GTA GAA AGA GCA GCA CAG CTG GCC ATC AGA GTC ACC AAT CCC AAC GCC AGG CTA CGC AGC GAA GAA AAT GAG TAG ATGGCTTGTGTG
Ala Ile Val Glu Arg Ala Ala Gln Leu Ala Ile Arg Val Thr Asn Pro Asn Ala Arg Leu Arg Ser Glu Glu Asn Glu  ***
               3' - END                                   3250                                          3300
                         ↓CGTCGTATTTTCTATGTTTTTGGTAACTGGAGATTGTTCTTTCTGCTTGTTCTGGGGAGACAGCAGGGTTCAGAATCCCATG
CATGTTTTATGTTTAAATAAATCACAAAACCTGC                                                                  >>>>>>>>>>>>> <<< <<
               3350
<< <<<<<
CTAGTCTCTTGGCTGCAGGTGAAGAGGGGAAAGGCCTTGACCCTCTACAGTGTAGGTACACTTAGAGTCTGGGGACC
```

FIG. 1D

```
                  *          *          *          *          *          *
-539   ggatccggagacggtggacggtaccccgccggccccctgctcccgggtgtggccgggaag -479   ggtgcacctgggcctgaggcgtgcccatgtagggtcccggtcgttggacaagacttcgtt -419   tcccacgctctcatttcccgccccccgccctcggagtgtttccctgtcggtcGGTCGAtC
                                                              ‾‾‾‾‾‾‾‾
                                                                  A'
-359   gGtcgggaggtggggaccggcctgagctggatggtgtgtcctggattTTgGGGGAgccaa
       ‾‾                                             ‾‾‾‾‾‾‾‾‾‾
                                                         B'
-299   gtccccgtctggagctccggacagaccgatacctgcccgcgtgggcaagccgggaagggc
                                                                 +1'
-239   ttcccggctggccggccggctccacctccttcatgtccctgtcccttcccTGCgGtCACG
                                                         ‾‾‾‾‾‾‾‾‾‾
                                                               C'
-179   CTccccgGGTCGACCAGatggctctgagagcgctgggtctggcgactctagggcagggcT
       ‾‾‾‾‾‾‾‾‾‾‾‾‾‾‾‾‾                                           ‾
              A
-119   gGGGGACAagtgtccggatgggggttccggggatacccccacgtcctgtgggtgggcccc
       ‾‾‾‾‾‾‾
          B                                                       +1
 -59   gctgctgggcatggacattttcgcggccgaaatacgccttttctgtcaccaggtagaTG
                                                                 ‾‾
  +2   CTGACACGaTcctcttcagcgcctgtcgctggagaccttgggcctctggatgcacgtggg
       ‾‾‾‾‾‾‾‾‾‾
           C
 +62   gggctttgggctttcggctgctgtccaaggcctgaccctgcccttcacccccgcgtggg +122   gccgctcgcctgggcctgtgcgccggctctcacttgtgcatccagctggcccgtgctgcg +182   gtgtctcctccggtctctggct  203
```

FIG. 2

VECTORS

This invention was made with government support under DK02438 awarded by NIH.

FIELD OF THE INVENTION

The invention relates to improved vectors, and more specifically, improved adenovirus vectors useful for gene therapy.

BACKGROUND

Adenoviruses (Ad) are double-stranded DNA viruses. The genome of adenoviruses (~36 kb) is complex and contains over 50 open reading frames (ORFs). These ORFs are overlapping and genes encoding one protein are often embedded within genes coding for other Ad proteins. Expression of Ad genes is divided into an early and a late phase. Early genes are those transcribed prior to replication of the genome while late genes are transcribed after replication. The early genes comprise E1a, E1b, E2a, E2b, E3 and E4. The E1a gene products are involved in transcriptional regulation; the E1b gene products are involved in the shut-off of host cell functions and MRNA transport. E2a encodes the a DNA-binding protein (DBP); E2b encodes the viral DNA polymerase and preterminal protein (pTP). The E3 gene products are not essential for viral growth in cell culture. The E4 region encodes regulatory protein involved in transcriptional and post-transcriptional regulation of viral gene expression; a subset of the E4 proteins are essential for viral growth. The products of the late genes (e.g., L1–5) are predominantly components of the virion as well as proteins involved in the assembly of virions. The VA genes produce VA RNAs which block the host cell from shutting down viral protein synthesis.

Adenoviruses or Ad vectors have been exploited for the delivery of foreign genes to cells for a number of reasons including the fact that Ad vectors have been shown to be highly effective for the transfer of genes into a wide variety of tissues in vivo and the fact that Ad infects both dividing and non-dividing cells; a number of tissues which are targets for gene therapy comprise largely non-dividing cells.

The current generation of Ad vectors suffer from a number of limitations which preclude their widespread clinical use. The most serious limitation is the loss of expression of genes of interest in cells infected with Ad vectors. It has been assumed that this loss in expression is due to immune detection and elimination of cells infected with Ad vectors, but more recently transcriptional regulation has been raised as a potential factor in loss of transgene expression.

What is needed is an approach that overcomes the problem of loss of expression of genes of interest in cells infected with Ad vectors. Such an approach should ensure long-term expression for gene therapy and other applications.

SUMMARY OF THE INVENTION

The present invention contemplates improving vectors generally, and more specifically improving adenovirus vectors. The present invention contemplates both improved compositions (e.g., expression vectors) and methods (e.g., methods of transfection and gene therapy). With regard to compositions, the present invention contemplates an expression vector comprising a ribosomal promoter sequence operably linked to a gene of interest. The invention is not limited by the nature of the ribosomal promoter sequence chosen; any non-viral promoter sequence or portion thereof which is functional in cells (i.e., such that a gene of interest can be expressed and/or overexpressed) may be utilized. A variety of ribosomal promoters are known to those skilled in the art. Preferred ribosomal promoters are eukaryotic ribosomal promoters, including but not limited to mammalian ribosomal promoters such as those of mice, rats, rabbits, pigs and humans.

In a preferred embodiment, said expression vector further comprises viral nucleic acid. It is not intended that the expression vector be limited to a particular viral vector. In one embodiment, said expression vector further comprises adenoviral nucleic acid. Indeed, the present invention contemplates replication-defective adenoviral vectors comprising a ribosomal promoter sequence operably linked to a genetic cassette encoding one or more gene products. In a preferred embodiment, adenoviral vectors shown to be free of E1 function (e.g., by absence of replication on HeLA cells) are contemplated, such vectors comprising a ribosomal promoter sequence operably linked to a genetic cassette encoding one or more gene products.

The present invention also contemplates a mammalian cell line containing the above-described recombinant vector and integrated viral sequences expressing E1 function. It is preferred that said cell line is a 293-derived cell line.

With regard to methods of transfection, the present invention contemplates a method, comprising: a) providing: i) eukaryotic cells, ii) an expression vector comprising a ribosomal promoter sequence operably linked to a genetic cassette encoding one or more gene products; and b) introducing said expression vector into said cells. Again, in a preferred embodiment, said expression vector further comprises viral nucleic acid, such as adenoviral nucleic acid.

With regard to methods of gene therapy, in one embodiment, the present invention contemplates a method for delivering nucleic acid to cells of an animal, comprising: a) providing: i) an expression vector comprising a ribosomal promoter sequence operably linked to a gene of interest, ii) a recipient animal; and b) administering said vector to said recipient animal.

In a particular embodiment, the oligonucleotide or gene cassette is delivered to a particular tissue in said animal. It is not intended that the present invention be limited to the particular tissue type. In one embodiment, however, said tissue is selected from the group consisting of lung, trachea and liver tissue. For delivery to the liver, the hepatocytes can be readily transfected in vivo by direct vector infusion in the portal vein, as well as to the peripheral circulation.

With regard to other methods of gene therapy, in another embodiment, the present invention contemplates a method for delivering nucleic acid to cells of an animal, comprising: a) providing: i) an expression vector comprising a ribosomal promoter sequence operably linked to a gene of interest, ii) a recipient animal; b) coupling said expression vector to a carrier to generate a composition; and c) administering said composition to said recipient animal.

Where adenoviral vectors are employed in the present invention it is not intended that the present invention be limited by the precise size of the vector, although it is generally desirable that the vector have a total size of between 20 and 40 kilobase pairs. It is preferred that the total size of the DNA packaged into an adenovirus particle derived from these vectors is about the length of the wild-type adenovirus genome (~36 kb). It is well known in the art that DNA representing about 105% of the wild-type length may be packaged into a viral particle; thus the adenovirus particle derived from recombinant vector may contain DNA whose length exceeds by ~105% the size of the wild-type genome. The size of the recombinant plasmid may be adjusted using reporter genes and genes of interest having various sizes (including the use of different sizes of introns within these genes) as well as through the use of irrelevant or non-coding DNA fragment which act as "stuffer" fragments (e.g., portions of bacteriophage genomes).

In one embodiment, the present invention contemplates recovering said encapsidated adenovirus minichromosome and, in turn, purifying said recovered encapsidated adenovirus minichromosome. Thereafter, said purified encapsidated adenovirus minichromosome can be administered to a host (e.g., a mammal). Human therapy is thereby contemplated.

It is not intended that the present invention be limited by the nature of the administration of said adenovirus minichromosomes. All types of administration are contemplated, including direct injection (intramuscular, intravenous, subcutaneous, etc.), inhalation, etc.

BRIEF DESCRIPTION OF THE FIGURES

FIG. 1 SEQ ID NO: 1 shows mouse L32 ribosomal promoter sequences.

FIG. 2 SEQ ID NO: 2 shows pig ribosomal promoter sequences.

DEFINITIONS

Figure 3:
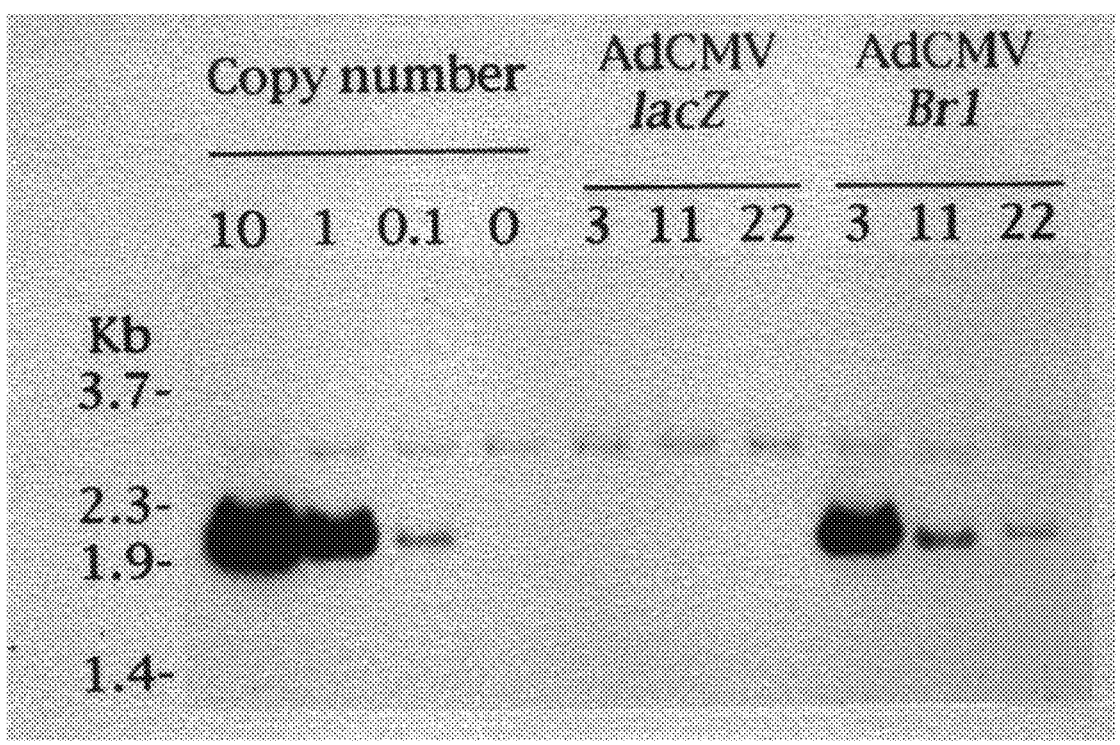
FIG. 3 shows the results of in vivo transfection of liver of recipient animals (with a vector comprising a viral promoter) by Southern analysis.

To facilitate understanding of the invention, a number of terms are defined below.

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained. The term "gene" encompasses both cDNA and genomic forms of a given gene.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined below).

Transcriptional control signals in eucaryotes comprise "promoter" and "enhancer" elements. Promoters and enhancers consist of short arrays of DNA sequences that interact specifically with cellular proteins involved in transcription [Maniatis, T. et al., Science 236:1237 (1987)]. Promoter and enhancer elements have been isolated from a variety of eukaryotic sources including genes in yeast, insect and mammalian cells and viruses (analogous control elements, i.e., promoters, are also found in procaryotes).

The term "heterologous DNA sequence" refers to a nucleotide sequence which is not endogenous to the cell into which it is introduced. Heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. An example of heterologous DNA of the present invention comprises a heterologous regulatory sequence such as a heterologous ribosomal promoter which is not found in the mammalian cell into which it is introduced. However, the present invention also contemplates endogenous (also called "homologous") ribosomal promoters in operable combination with heterologous genes of interest.

The term "recombinant DNA vector" as used herein refers to DNA sequences containing a desired coding sequence and appropriate DNA sequences necessary for the expression of the operably linked coding sequence in a particular host organism (e.g., mammal). DNA sequences necessary for expression in procaryotes include a promoter, optionally an operator sequence, a ribosome binding site and possibly other sequences. Eukaryotic cells are known to utilize promoters, polyadenlyation signals and enhancers.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "genetic cassette" as used herein refers to a fragment or segment of DNA containing a particular grouping of genetic elements. The cassette can be removed and inserted into a vector or plasmid as a single unit. A "plasmid backbone" refers to a piece of DNA containing at least plasmid origin of replication and a selectable marker gene (e.g., an antibiotic resistance gene) which allows for selection of bacterial hosts containing the plasmid; the plasmid backbone may also include a polylinker region to facilitate the insertion of genetic elements within the plasmid. When a particular plasmid is modified to contain non-plasmid elements (e.g. insertion of Ad sequences and/or a eukaryotic gene of interest linked to a ribosomal promoter), the plasmid sequences are referred to as the plasmid backbone.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to fmd each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modem biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art.

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single-or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "polymorphic locus" is a locus present in a population which shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, viruses, protozoans, flngi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery). Adenoviruses, as noted above, are double-stranded DNA viruses. The left and right inverted terminal repeats (ITRs) are short elements located at the 5' and 3' termini of the linear Ad genome, respectively and are required for replication of the viral DNA. The left ITR is located between 1–130 bp in the Ad genome (also referred to as 0–0.5 mu). The right ITR is located from ~3,7500 bp to the end of the genome (also referred to as 99.5–100 mu). The two ITRs are inverted repeats of each other. The 5' end of the left ITR is located at the extreme 5' end of the linear adenoviral genome; picturing the left ITR (LITR) as an arrow extending from the 5' end of the genome, the tail of the 5' ITR is located at mu 0 and the head of the left ITR is located at ~0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at ~mu 99.5; the head of the right ITR is referred to as the 5' end of the right ITR and the tail of the right ITR is referred to as the 3' end of the right ITR (RITE). In the linear Ad genome, the ITRs face each other with the head of each ITR pointing inward toward the bulk of the genome. When arranged in a "tail to tail orientation" the tails of each ITR (which comprise the 5' end of the LITR and the 3' end of the RITE) are located in proximity to one another while the heads of each ITR are separated and face outward. The "adenovirus packaging sequence" refers to the $\Psi$ sequence which comprises five (AI–AV) packaging signals and is required for encapsidation of the mature linear genome; the packaging signals are located from ~194 to 358 bp in the Ad genome (about 0.5–1.0 mu).

The phrase "at least one adenovirus gene coding region" refers to a nucleotide sequence containing one or more than one adenovirus gene coding sequence. A "helper adenovirus" or "helper virus" refers to an adenovirus which is replication-competent in a particular host cell (the host may provide Ad gene products such as E1 proteins), this replication-competent virus is used to supply in trans functions (e.g., proteins) which are lacking in a second replication-incompetent virus; the first replication-competent virus is said to "help" the second replication-incompetent virus thereby permitting the propagation of the second viral genome in the cell containing the helper and second viruses.

The term "containing a deletion within the E1b region" refers to a deletion of at least one basepair (preferably more than one bp and preferably at least 100 and most preferably more than 300 bp) within the E1b region of the adenovirus genome. An E1b deletion is a deletion that prevents expression of at least one E1b gene product. In a preferred embodiment, the present invention contemplates a vector wherein the sequences spanning the E1a, E1b and E3b regions are deleted.

An "adenovirus minichromosome" refers to a linear molecule of DNA containing the Ad ITRs on each end which is generated from a plasmid containing the ITRs and one or more gene of interest. The term "encapsidated adenovirus minichromosome" or "EAM" refers to an adenovirus minichromosome which has been packaged or encapsidated into a viral particle. When used herein, "recovering" encapsidated adenovirus minichromosomes refers to the collection of EAMs from a cell containing an EAM plasmid and a helper virus; this cell will direct the encapsidation of the minichromosome to produce EAMs. The EAMs may be recovered from these cells by lysis of the cell (e.g., freeze-thawing) and pelleting of the cell debris to a cell extract. "Purifying" such minichromosomes refers to the isolation of the recovered EAMs in a more concentrated form (relative to the cell lysate) using techniques such as on a density gradient; purification of recovered EAMs permits the physical separation of the EAM from any helper virus (if present).

The term "transfection" as used herein refers to the introduction of foreign DNA into eukaryotic cells. Transfection may be accomplished by a variety of means known to the art including calcium phosphate-DNA co-precipitation, DEAE-dextranmediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "long-term expression" as used herein means detectable expression for more than six (6) months and, more preferably, more than one (1) year, following transfection of cells in an immunocompetent (i.e., not immunocompromised) animal.

As used herein, the term "gene of interest" refers to a gene inserted into a vector or plasmid whose expression is desired in a host cell. Genes of interest include genes having therapeutic value as well as reporter genes. A variety of such genes are contemplated, including genes of interest encoding a protein which provides a therapeutic function. It is not intended that the present invention be limited to genes of interest encoding a particular protein having therapeutic function. A variety of such genes are contemplated including but not limited to the bilirubin UDP-glucuronosyltransferase gene, the dystrophin gene (which is capable of correcting the defect seen in the muscle of MD patients), the utrophin gene, the CFTR gene (capable of correcting the defect seen in cystitic fibrosis patients), the genes encoding enzymes (particular enzymes associated with enzyme deficiency diseases or diseases known to be caused by enzyme defects) and genes encoding clotting factors, angiogenesis factors, anti-angiogenesis factors, tumor suppressors, and suicide genes of which the Herpes thymidine kinase gene is an example. Genes of interest can be both endogenous and heterologous.

The term "reporter gene" indicates a gene sequence that encodes a reporter molecule (including an enzyme). A "reporter molecule" is detectable in any detection system, including, but not limited to enzyme (e.g., ELISA, as well as enzyme-based histochemical assays), fluorescent, radioactive, and luminescent systems. In one embodiment, the present invention contemplates the E. coli $\mu$-galactosidase gene (available from Pharmacia Biotech, Pistacataway, N.J.), green fluorescent protein (GFP) (commercially available from Clontech, Palo Alto, Calif.), the human placental alkaline phosphatase gene, the chloramphenicol acetyltransferase (CAT) gene; other reporter genes are known to the art and may be employed (e.g., to easily follow success in transfection).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DESCRIPTION OF THE INVENTION

The present invention provides improved vectors, and in particular improved adenovirus vectors, for the delivery of recombinant genes to cells in vitro and in vivo. The description of the invention includes: A) selection of a ribosomal promoter; B) design of the expression vector; and C) delivery of the vector.

A. Selection of a Ribosomal Promoter

The present invention contemplates an expression vector comprising a ribosomal promoter sequence operably linked to a gene of interest. The invention is not limited by the nature of the ribosomal promoter sequence chosen; any non-viral promoter sequence or portion thereof which is functional in cells (i.e., such that a gene of interest can be expressed and/or overexpressed) may be utilized. A variety of ribosomal promoters are known to those skilled in the art.

The nucleotide sequences for such ribosomal promoters are known and available from the GenBank/EMBL database: *Homo sapiens* (X01547), *Rattus norvegicus* (X00677, K01588, M12030), *Xenopus laevis* (J01005), *Xenopus borealis* (X05263, Y00132, X00184), *Drosophila melanogaster* (X02210), *Paracentrotus lividus* (X63234), *Tetrahymena pyriformis* (J01212, M10096), *Dictyostelium discoideum* (X00601), *Arabidopsis thaliana* (X15550), *Pisum sativum* (X52575), *Triticum aestivum* (X07841), *Zea mays* (X03990).

B. Design of the Vector

It is not intended that the present invention be limited to a particular vector. Both viral vectors and non-viral vectors are contemplated. In a preferred embodiment, adenovirus vectors are employed.

1. Adenovirus Vectors

Self-propagating adenovirus (Ad) vectors have been extensively utilized to deliver foreign genes to a great variety of cell types in vitro and in vivo. "Self-propagating viruses" are those which can be produced by transfection of a single piece of DNA (the recombinant viral genome) into a single packaging cell line to produce infectious virus; self-propagating viruses do not require the use of helper virus for propagation.

Existing Ad vectors have been shown to be problematic in vivo. This is due in part because current or first generation Ad vectors are deleted for only the early region 1 (E1) genes, as well as to the fact that viral regulatory units such as the CMV promoter/enhancer are inactivated over time. These vectors are crippled in their ability to replicate normally without the trans-complementation of E1 functions provided by human 293 cells, a packaging cell line [ATCC CRL 1573; Graham et al (1977) *J. Gen. Virol.* 36:59]. Unfortunately, with the use of high titres of E1 deleted vectors, and the fact that there are E1-like factors present in many cell types, E1 deleted vectors can overcome the block to replication and express other viral gene products [Imperiale et al (1984) *Mol. Cell Biol.* 4:867; Nevins (1981) *Cell* 26:213; and Gaynor and Berk (1983) Cell 33:683]. The expression of viral proteins in the infected target cells elicits a swift host immune response, that is largely T-cell mediated [Yang and Wilson (1995) *J Immunol.* 155:2564 and Yang et al. (1994) *Proc. Natl. Acad. Sci. USA* 91:4407]. This immune response leads to changes in cytokine gene expression which can turn off transgenic expression when viral promoters are used. See L. Qin et al., "Promoter Attention in Gene Therapy: Interferon-γ and Tumor Necrosis Factor-α Inhibit Transgene Expression," *Human Gene Therapy* 8:2019 (1997).

Figure 1B:
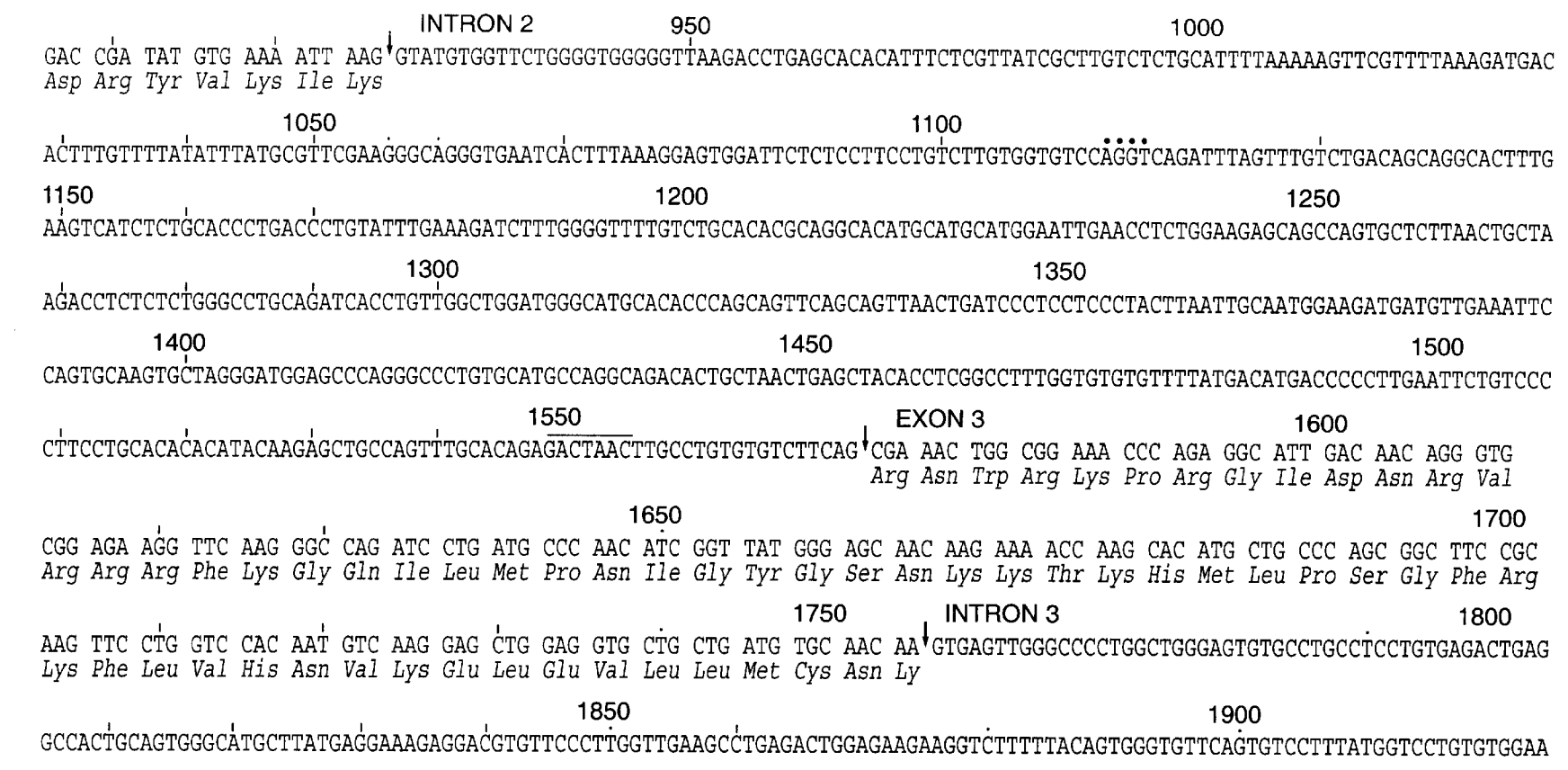

The present invention contemplates adenovirus vectors employing novel endogenous promoter elements which are not inactivated by the immune response. Suitable adenovirus vectors are described in U.S. Pat. No. 5,585,362 to Wilson et al., entitled "Adenovirus Vectors For Gene Therapy," hereby incorporated by reference. In one embodiment, the present invention contemplates a vector wherein mouse L32 ribosomal promoter sequences (FIG. 1) SEQ ID NO: 1 are used to regulate transgene expression, leading to persistence of expression for one year or more.

2. Other Viral Vectors

It is not intended that the present invention be limited to adenoviral vectors. A variety of other viral vectors are contemplated, including but not limited to lentiviral vectors, AAV (adeno-associated virus) vectors, retrovirus vectors, and herpes virus vectors.

C. Delivery Of The Vector

Functional exogenous genes can be introduced to mammalian cells in vitro by a variety of physical methods, including transfection, direct microinjection, electroporation, and coprecipitation with calcium phosphate. While satisfactory for transfecting cells in culture, most of these techniques, however, are impractical for delivering genes to cells within intact animals. The present invention contemplates the use of viral vectors, as well as non-viral vectors for delivery of nucleic acid comprising a ribosomal promoter in operable combination with a gene of interest.

It is not intended that the present invention be limited to just one delivery approach. Exemplary delivery approaches are discussed below.

1. Receptor-Mediated Uncompacted DNA Delivery In Vivo

Receptor-mediated gene transfer has been shown to be successful in introducing transgenes into suitable recipient cells, both in vitro and in vivo. This procedure involves linking the DNA to a polycationic protein (usually poly-L-lysine) containing a covalently attached ligand, which is selected to target a specific receptor on the surface of the tissue of interest. The gene is taken up by the tissue, transported to the nucleus of the cell and expressed for varying times. The overall level of expression of the transgene in the target tissue is dependent on several factors: the stability of the DNA-carrier complex, the presence and number of specific receptors on the surface of the targeted cell, the receptor-carrier ligand interaction, endocytosis and transport of the complex to the nucleus, and the efficiency of gene transcription in the nuclei of the target cells.

Wu et al., U.S. Pat. No. 5,166,320 (hereby incorporated by reference), discloses tissue-specific delivery of DNA using a conjugate of a polynucleic acid binding agent (such as polylysine, polyarginine, polyornithine, histone, avidin, or protamine) and a tissue receptor-specific protein ligand. For targeting liver cells, Wu suggests "asialoglycoprotein (galactose-terminal) ligands".

Wagner, et al., *Proc. Natl. Acad. Sci.*, 88:4255–4259 (1991) and U.S. Pat. No. 5,354,844 (hereby incorporated by reference) disclose complexing a transferrin-polylysine conjugate with DNA for delivering DNA to cells via receptor mediated endocytosis. Wagner, et al, teach that it is important that there be sufficient polycation in the mixture to ensure compaction of plasmid DNA into toroidal structures of 80–100 nm diameter, which, they speculate, facilitate the endocytic event.

2. Direct Injection Of Naked, Uncompacted DNA

The possibility of detecting gene expression by directly injecting naked DNA into animal tissues was demonstrated first by Dubenski et al, *Proc. Nat. Acad. Sci. USA*, 81:7529–33 (1984), who showed that viral or plasmid DNA injected into the liver or spleen of mice was expressed at detectable levels. The DNA was precipitated using calcium phosphate and injected together with hyaluronidase and collagenase. The transfected gene was shown to replicate in the liver of the host animal. Benvenisty and Reshef, *Proc. Nat. Acad. Sci. USA*, 83:9551–55 (1986) injected calcium phosphate precipitated DNA intraperitoneally into newborn rats and noted gene expression in the livers of the animals 48 hours after transfection. In 1990, Wolff et al, *Science*, 247:1456–68 (1990), reported that the direct injection of DNA or RNA expression vectors into the muscle of mice resulted in the detectable expression of the genes for periods for up to 2 months. This technique has been extended by Acsadi et al., *New Biologist*, 3:71–81 (1991) to include direct injection of naked DNA into rat hearts; the injected genes were expressed in the heart of the animals for up to 25 days. Other genes, including the gene for dystrophin have been injected into the muscle of mice using this technique. This procedure forms the base of a broad approach for the generation of immune response in an animal by the administration of a gene by direct injection into the target tissue. The gene is transiently expressed, producing a specific antigen. (See Donnelly et al., *The Immunologist*, 21, pp. 20–26 (1994) for a recent review). However, the DNA used in these experiments has not been modified or compacted to improve its survival in the cell, its uptake into the nucleus or its rate of transcription in the nucleus of the target cells.

3. Administration of Viral Vectors In The Portal Vein

In a particular embodiment, the genetic cassette is delivered to a particular tissue in said animal. It is not intended that the present invention be limited to the particular tissue type. In one embodiment, however, said tissue is selected from the group consisting of lung, trachea and liver tissue. For delivery to the liver, the hepatocytes can be readily transfected in vivo by direct vector infusion in the portal vein, as well as to the peripheral circulation.

DESCRIPTION OF SPECIFIC EMBODIMENTS

One hepatic metabolic deficiency that has attracted broad interest due to the hope that it might be cured by gene therapy is Crigler-Najar syndrome type I, familial non-hemolytic jaundice with kernicterus. Crigler-Najar syndrome is an autosomal recessive inherited metabolic defect in bilirubin glucuronosyltransferase activity. Patients with Crigler-Najjar syndrome type I do not conjugate bilirubin and a striking unconjugated hyperbilirubinemia develops, leading to kernicterus and death, usually in infancy or childhood. Patients with one normal allele have an essentially normal phenotype suggesting that partial genetic correction may lead to a functional cure in Crigler-Najjar type I patients. The usual treatments for Crigler-Najjar syndrome, phototherapy and pharmacologic treatment, are not adequate to keep patients with type I disease alive. Crigler-Najjar syndrome type I patients theoretically are ideal candidates for liver directed human gene therapy trials as complementation of a genetic enzymatic defect has the theoretic potential to cure disease before the sequela of kernicterus leads to death.

The human bilirubin UDP-glucuronosyltransferase gene locus (UGT1) encodes multiple glucuronosyltransferases generated by alternately splicing variable 5' introns (and the corresponding exons) with a common 3' region consisting of exons 2–5. Complementation of the genetic deficiency in primary and immortalized Gunn rat hepatocytes with retroviruses and plasmids has demonstrated the ability of HUG Br 1 and HUG Br 2 vectors to express bilirubin UDP-glucuronosyltransferase activity in these cells. Human fibroblasts derived from a Crigler-Najjar patient have also been shown to express bilirubin glucuronosyltransferase activity following HUG Br 1 gene transfer. The presence of multiple bilirubin UDP-glucuronosyltransferase isoforms raised the question as to whether gene transfer of a single isoform could correct the Crigler-Najjar phenotype in vivo.

One feature which makes Crigler-Najjar syndrome type I attractive to study is the availability of an authentic animal model of the human disease, the Gunn rat. The majority of bilirubin UDP-glucuronosyltransferase activity is normally expressed in the liver, and hepatocytes are therefore a logical target to treat this disease. The present invention describes in vivo adenovirus-mediated gene transfer of the genetic cassette encoding the major human bilirubin UDP-glucuronosyltransferase isoform, HUG Br 1, to complement the genetic deficiency in Gunn rat hepatocytes.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); $\mu$M (micromolar); mol (moles); mmol (millimoles); $\mu$mol (micromoles); nmol (nanomoles); mu or m.u. (map unit); g (gravity); gm (grams); mg (milligrams); $\mu$g (micrograms); pg (picograms); L (liters); ml (milliliters); $\mu$l (microliters); cm (centimeters); mm (millimeters); $\mu$m (micrometers); nm (nanometers); hr (hour); min (minute); msec (millisecond); ° C. (degrees Centigrade). LP-293 cells (Microbix Biosystems, Toronto) were grown and serially passaged as suggested by the supplier.

EXAMPLE 1

Gene Therapy Using The CMV Promoter

In this example, the in vivo glucuronosyltransferase activity conferred by an adenoviral vector comprising a viral promoter in operable combination with a gene of interest is assessed. The gene of interest used herein for illustrative purposes is the bilirubin UDP-glucuronosyltransferase gene ("HUGBr1").

The cellular localization of MRNA expression was analyzed in livers infused with replication-defective adenoviral vectors based on an AdS sub360 serotype viral genomic backbone which is deleted of sequences spanning the E1a, E1b, and E3b regions, with the E1 deletions resulting in the impaired ability of this virus to replicate in non-permissive cells.3 The cytomegalovirus immediate early promoter and enhancer were cloned into the parent plasmid pAdBg1 II to generate the proviral plasmid which was then used to make the HUG Br 1 adenovirus vector used herein.

Following homologous recombination (within 9.2 to 16.1 map units), E1a/E1b deleted recombinant adenoviral clones containing the HUG Br 1 cDNA were produced. The identity of recombinant clones was verified by restriction analysis of viral DNA minipreps and Southern blot analysis, and all vectors were purified through two rounds of plaque purification and assayed for titer by limiting dilution plaque assay on 293 cells.

High titer suspensions of recombinant adenovirus were prepared by amplification in 293 cells using established methods. Virus was purified from cell lysates by cesium chloride gradient ultra-centrifugation followed by de-salting by dialysis to HBS. Purified virus was used immediately for in vivo injections. Titers were determined by O.D.260 and standard plaque assay, and were approximately $1\times10^{13}$ particles/mL ($1\times10^{11}$ plaque-forming units/mL). As a control, the previously categorized adenovirus H5.010CMVlacZ. was used. All adenoviral preparations were shown to be free of E1 function by absence of replication on HeLa cells, and PCR amplification of the E1 region was performed to exclude reconstitution of the E1 genome from 293 cells in the prepared vectors (data not shown).

Animal experiments were performed in accordance with institutional guidelines. Adult 200 gm Gunn rats were anesthetized with ketamine/rompun, and the abdominal area was scrubbed with povidone/iodine. Using sterile technique and a midline approach, $5 \times 10^9$ pfu of adenoviral vector suspension in HBS was infused into the portal vein. Six animals were infused with H5.010CMVlacZ (the vector comprising a reporter gene as the gene of interest) and nine animals were infused with H5.010CMVhugBr1 (the vector comprising the transferase gene as the gene of interest). Pressure was applied for five minutes to achieve hemostasis.

At 3 days, 11 days, and 22 days post infusion two animals from each group were anesthetized, and bile collected prior to euthanasia. Livers were divided with samples from each lobe frozen on liquid nitrogen and stored at $-80°$ C. until analysis. Liver samples were analyzed for the presence of vector DNA and transgene expression.

Southern blot hybridization was performed as follows. Samples were restricted with Bam H1 and probed with a random primer labeled 0.7 kilobase (kb) BAM/ECO R1 fragment of pcDNAHUG Br 1. The results are shown in FIG. 3. The first four lanes contain DNA (10 μg) from mock infused livers supplemented with copy number controls: 1) ten copy number (75 pg of pAdCMVHUGBr1); 2) one copy number (7.5 pg of pAdCMVHUGBr1); 3) 0.1 copy number (0.75 pg of pAdCMVHUGBr1); and 4) 0 copy number. The next three lanes (5,6 and 7) represent genomic DNA (10 μg) from Gunn rat livers transduced with H5.010CMVlacZ 3, 11, and 22 days post infusion as labeled. Finally, the last three lanes (8, 9 and 10) contain genomic DNA (10 μg) from Gunn rat livers transduced with H5.010CMVhugBr1 3, 11, and 22 days post infusion, respectively, as labeled. The sequence-specific bands appeared at the predicted MW, 2100 bp. Hybridization noted with higher molecular weight sequences in control and experimental animals likely reflects nonspecific hybridization with genomic DNA, potentially cross-hybridization of the human HUG Br 1 probe with a partially homologous Gunn rat locus.

From the data in FIG. 3 it is clear that adenoviral vector DNA and RNA were detected 3 days post injection and then diminished over three weeks. Southern hybridization demonstrated nonrearranged proviral sequences in Gunn rat livers infused via the portal vein with $5 \times 10^9$ plaque-forming units (pfi) of H5.010CMVhugBr1. Transduction efficiencies ranged from between 1 to 10 copy number at three days post infusion and diminished to approximately 0.1 copy number at 22 days consistent with the transient transfection capability of first generation adenoviral vectors. No bands hybridizing with the HUG Br 1 probe were detected in Gunn rat liver at 3, 10, or 22 days post-infusion with H5.010CMVlacZ although control infusions with the H5.010CMVlacZ adenovirus vector using equal doses (pfu) to the HUG Br 1 adenovirus vector demonstrated comparable transduction efficiencies as determined by β-galactosidase staining of cells (data not shown).

EXAMPLE 2

Gene Therapy Using A Ribosomal Promoter

In this example, the in vivo glucuronosyltransferase activity conferred by an adenoviral vector comprising a ribosomal promoter in operable combination with a gene of interest is assessed. The gene of interest used herein for illustrative purposes is the bilirubin UDP-glucuronosyltransferase gene ("HUGBr1").

Figure 4:
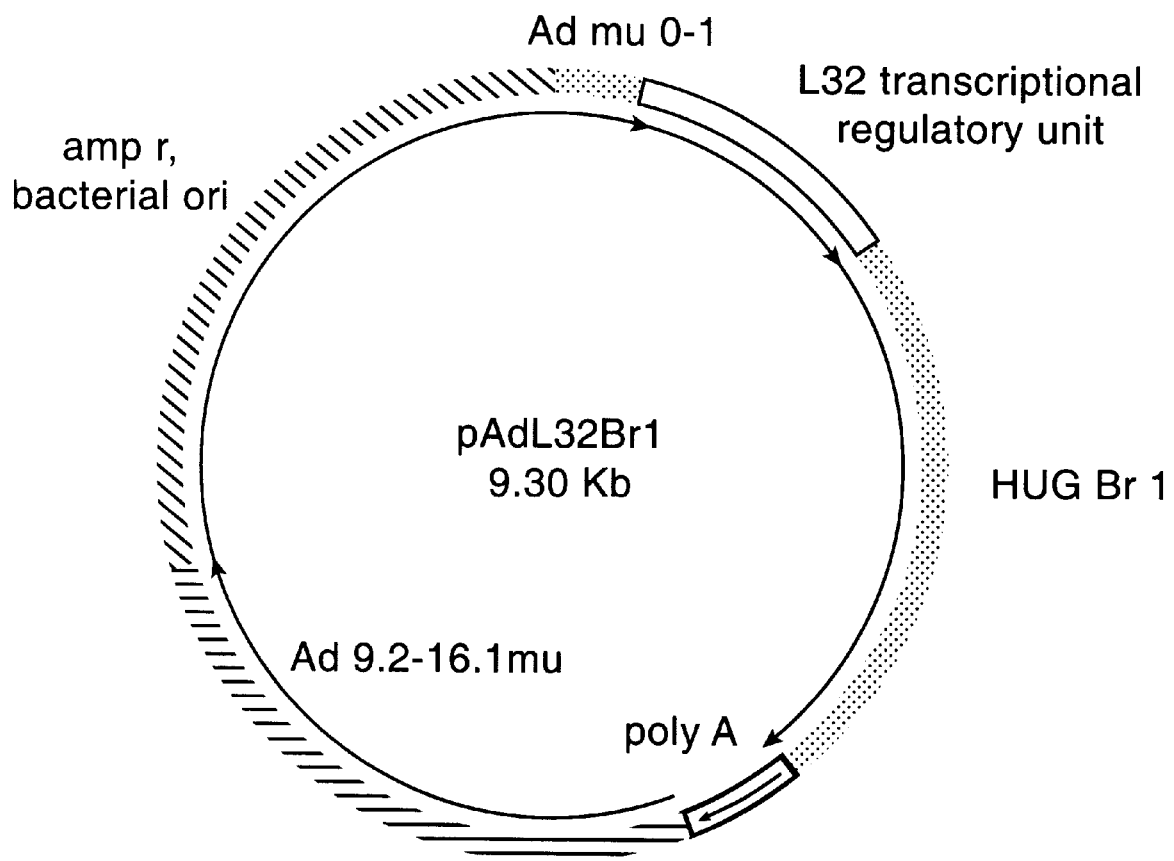
FIG. 4 shows a restriction map of an adenoviral vector comprising a ribosomal promoter in operable combination with a gene of interest. The plasmid is 9.30 kb; "amp r" refers to the ampicillin resistance gene and "bacterial ori" refers to the bacterial origin of replication. Human adenovirus type 5 sequences are denoted as map units (m.u.; 1 m.u.=360 bp).

The cellular localization of MRNA expression was analyzed in livers infused with replication-defective adenoviral vectors. FIG. 4 shows the restriction map of the adenoviral vector comprising the mouse L32 ribosomal promoter sequences in operable combination with the transferase gene.

Figure 5:
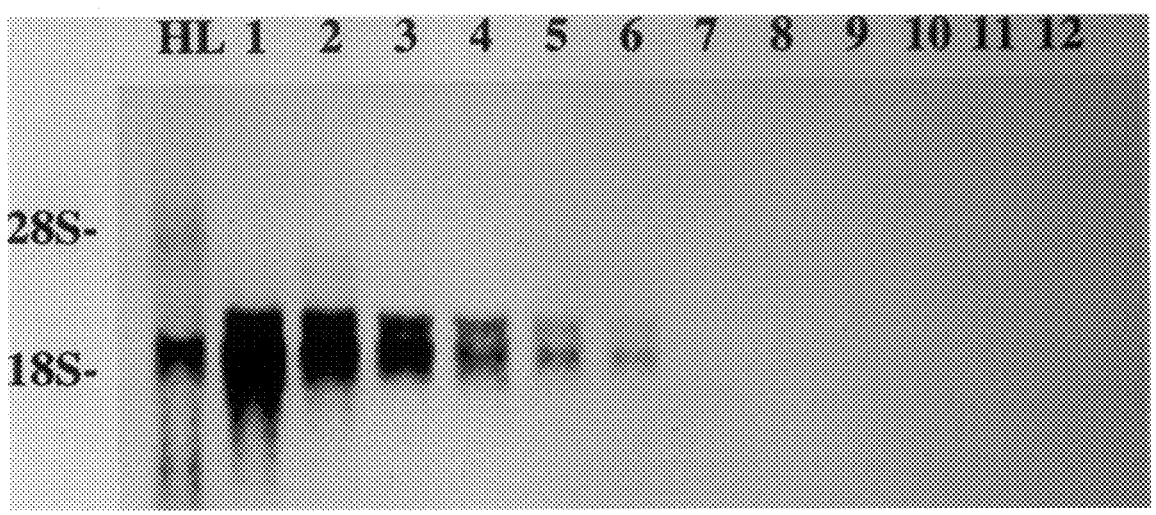
FIG. 5 shows the results of in vivo transfection of liver of recipient animals (with a vector comprising a ribosomal promoter) by Northern analysis.

In the manner set forth in Example 1 above, the adenoviral vector comprising the ribosomal promoter was infused into the portal vein of recipient animals (and other animals received the vector comprising the reporter gene), and the animals were sacrificed at various time points. The liver samples were analyzed for the presence of vector DNA and transgene expression as follows. RNA was extracted, electrophoresed, and hybridized with the probe described above. FIG. 5 shows the results by Northern analysis. The far left lane contains positive control RNA derived from normal human liver. The next six lanes (#1–6) contain RNA from livers 3, 10, 21, 188, 274 and 358 days post transduction with the vector comprising the ribosomal promoter in operable combination with the gene of interest (i.e., the transferase gene). The final six lanes (#7–12) contain total cellular RNA derived from Gunn rat livers 3, 10, 21, 188, 274 and 358 days post transduction with the vector comprising the ribosomal promoter in operable combination with the reporter gene.

The results show sequence specific hybridization to human liver RNA and, most importantly, the persistence of expression over time. The migration of ribosomal RNAs is indicated along the lefthand border.

Figures 6A, 6B:
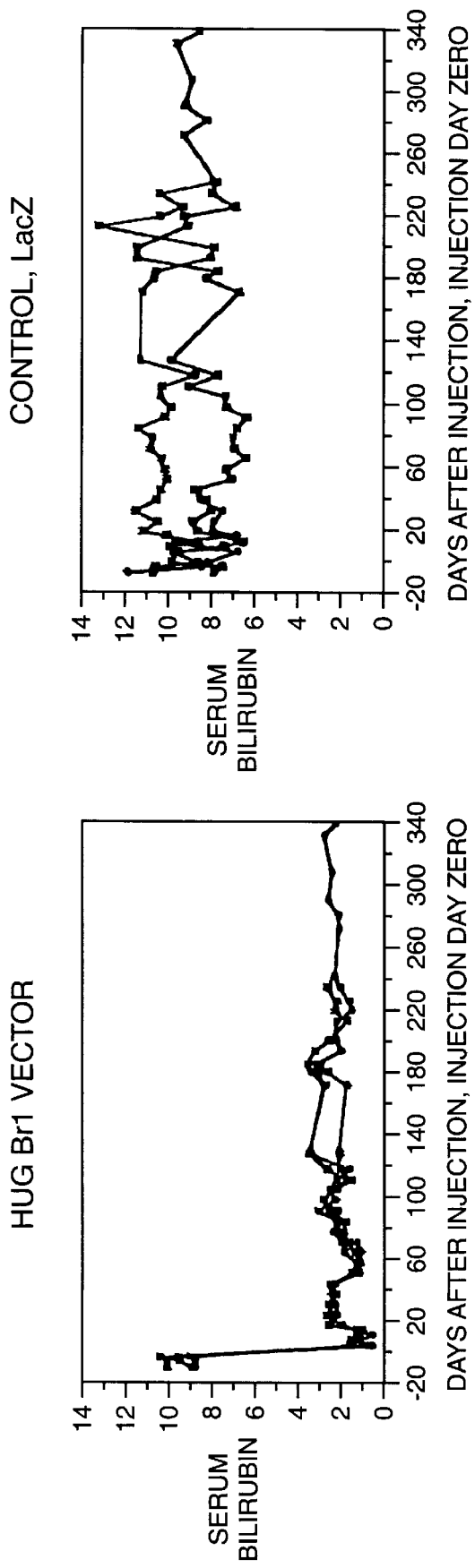
FIG. 6A and 6B show the bilirubin levels of control (Panel B) and treated (Panel A) animals following transfection with a vector comprising a ribosomal promoter.

FIG. 6 shows serum bilirubin levels in Gunn rats infused with a vector comprising a ribosomal promoter in operable combination with (A) the transferase gene and (B) the reporter gene. Three time pints were drawn for each animal over ten days prior to injection, which is plotted as day zero. Serum bilirubin values were taken at the specified times for up to 356 days in experimental and control groups, with three animals in each group followed. Total serum bilirubin was determined by spectrophotometric analysis of diazo bilirubin derivatives.

The results show significant differences between the control (B) and the treatment group (A). In the treatment group, serum bilirubin levels fell to within normal limits, with the standard deviation of post-infusion values in comparison to pre-infusion bilirubin values significantly decreased ($p<0.05$). There was no significant drop in the bilirubin levels in any of the animals in the control group (B).

Figure 7A:
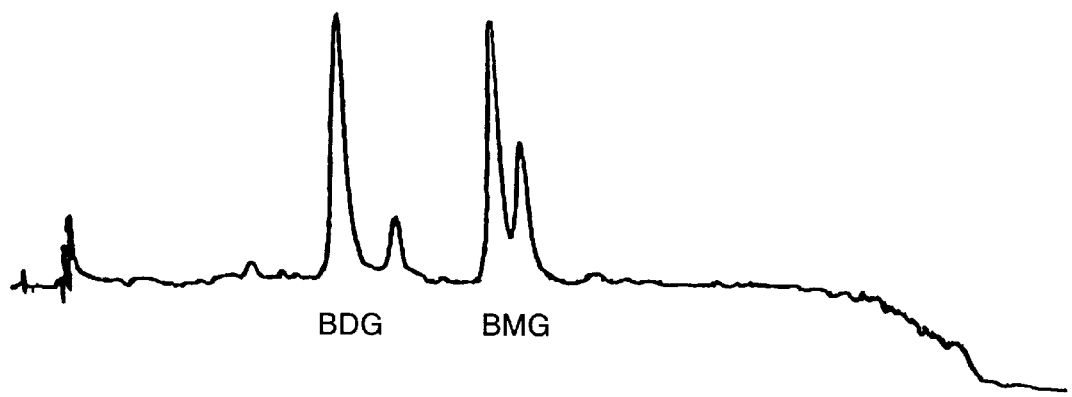
FIG. 7A, 7B, and 7C are graphs showing HPLC analysis of bile for bilirubin glucuronides in untreated animals (A), and animals transfected with the transferase gene (B) or a reporter gene (C).
Figure 7B:
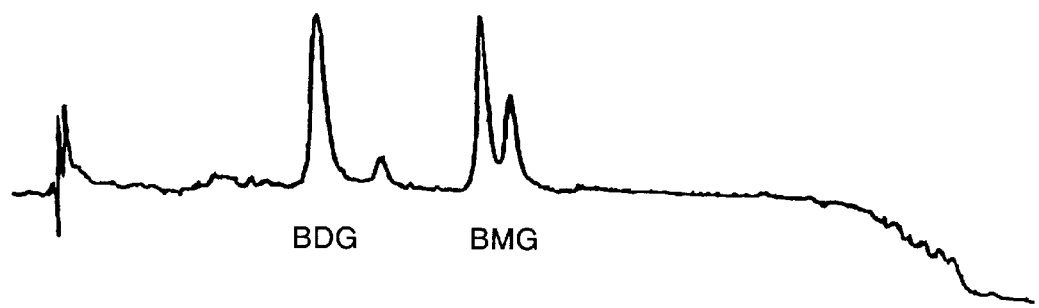
Figure 7C:

FIG. 7 shows HPLC analysis of bile for bilirubin glucuronides. The panel on the top (A) is a representative HPLC tracing of bile collected from a Wistar rat. Bilirubin glucuronides are distributed relative evenly between mono-(BMG) and di-(BDG) glucuronides. The middle panel (B) is a representative HPLC tracing from a Gunn rate 358 days following transduction with the vector comprising the ribosomal promoter in operable combination with the transferase gene (bile from each animal was analyzed in triplicate). Finally, on the bottom panel (C), no bilirubin glucuronides are evident in bile collected from a Gunn rat which received the control vector. Care was taken to avoid light exposure in all samples.

Figure 8:
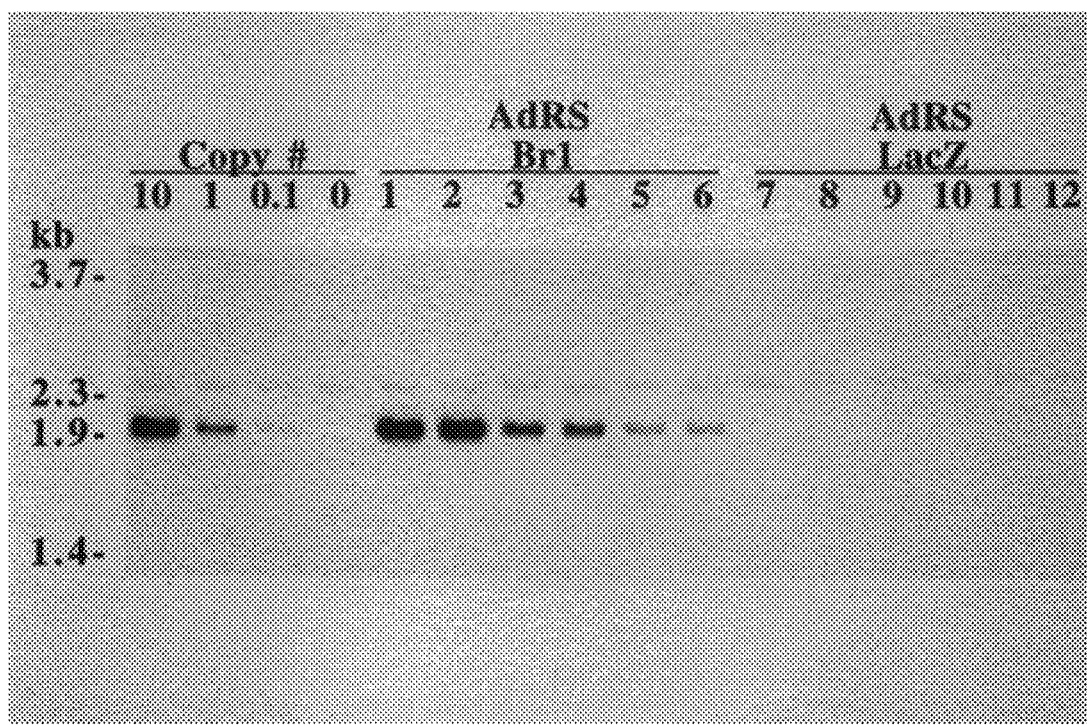
FIG. 8 shows the results of in vivo transfection of liver of recipient animals (with a vector comprising a ribosomal promoter) by Southern analysis.

FIG. 8 shows the results from Southern blot hybridization, where total cellular DNA was probed for HUG Br 1. All lanes contain genomic DNA (10 μg) from Gunn rat livers.

The first four lanes contain DNA (10 μg) from mock infused livers supplemented with copy number controls: 1) ten copy number (75 pg of pAdL32HUGBr1); 2) one copy number (7.5 pg of pAdL32HUGBr1); 3) 0.1 copy number (0.75 pg of pAdL32HUGBr1); and 4) 0 copy number. The next six lanes (#1–6) represent DNA from livers 3, 10, 21, 188, 274 and 358 days post-transduction with AdL32hugBr1 (labelled AdRSBr1). The final six lanes (#7–1) represent DNA from livers 3, 10, 21, 188, 274 and 358 days post-transduction with AdL321acZ (labelled AdRSLacZ). The migration of molecular weight markers is indicated along the lefthand border. The sequence-specific bands appeared at the predicted MW, 2100 bp. Hybridization noted with higher molecular weight sequences in control and experimental animals likely reflects nonspecific hybridization with genomic DNA, potentially cross-hybridization of the human HUG Br 1 probe with a partially homologous Gunn rat locus.

The results in FIG. 8 show sequence specific hybridization. Most importantly, the results show persistent expression over time.

From the above, it should be clear that there are advantages to a vector comprising a ribosomal promoter in operable combination with a gene of interest, as compared to vectors with standard promoters (CMV promoter). In vivo transfection with the appropriate gene of interest results in persistent expression over time, offering the opportunity to treat disease and disease sequelae in a long-term fashion.

What is claimed is:

1. A composition comprising an adenoviral expression vector, said vector comprising a ribosomal promoter sequence operably linked to a heterologous gene of interest.

2. The composition of claim 1, further comprising an animal cell, wherein said vector is in said animal cell and said animal cell expresses said gene of interest.

3. The composition of claim 1, wherein said ribosomal promoter sequence comprises a eukaryotic ribosomal promoter sequence.

4. The composition of claim 3, wherein said eukaryotic ribosomal promoter sequence comprises a mammalian ribosomal promoter sequence.

5. A composition comprising an adenoviral vector, said adenoviral vector comprising a ribosomal promoter sequence operably linked to a genetic cassette encoding one or more gene products.

6. The composition of claim 5, further comprising an animal cell wherein said vector is in said animal cell and said animal cell expresses said gene of interest.

7. The composition of claim 5, wherein said ribosomal promoter sequence comprises a eukaryotic ribosomal promoter sequence.

8. The composition of claim 7, wherein said eukaryotic ribosomal promoter sequence comprises a mammalian ribosomal promoter sequence.

9. The composition of claim 1, wherein said adenoviral expression vector is free of E1 function.

10. A method for expressing a gene of interest comprising:
    (a) providing:
        i) eukaryotic cells,
        ii) an adenoviral expression vector comprising a ribosomal promoter sequence operably linked to a heterologous gene of interest; and
    (b) introducing said adenoviral expression vector into said cells in vitro.

11. The method of claim 10, wherein said gene of interest comprises a reporter gene.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3756 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "DNA"

(xi) SEQUENCE DESCRIPTION: SEQ ID NO:1:

```
GAGTCTCTGT TTTGCTACCT CCCAGCCTCA AGGAGGCACC CTCGGGAACC AACAATTTAA      60

AAAGCTATTG GGCTTCCACT TAGGGCGGAA ATAAATGCCC ACCTAGCAGG TCTTAGCTCA     120

AAAAAAAACA AAAAACCCAA ATTTCTTAAG TAGTCCCAAG AGAAAAATAA ATTTTAGTTC     180

ACTCTAAGAT GTTAATGTCT ACTACAGAAC ACTAGTCCAC TAGGGTTTTT TTCAGTATCA     240

TTTCTCAGGC ACATCTTAGT TTTCTTTAGA GGACCCAGAG CCGGAAGTGC TTCCCTTTTC     300

TCTGCTAGGA CCTAAGACTC CGTCCCATCA TACCTTGCGC GCCGCCGCCG CCTCTTCCTT     360

CTTCCTCGGC GCTGCCTACG AGGTGGCTGC CATCTGTTTT ACGGTGAGTC TGTATCGGCG     420

GCCATCCGCC GCCCGCGGCT TCGACGGGAC CCCGTCTCCG GGTGGGGAGG CCTCGGCGGC     480

GGCCTCCGCA CCAGCGTGGT AGTGGCGAGC GCGCGCGGGC CTGCCACTGG CGCTGCTCCG     540

GAGTCTGCCC GGGTCGGCAT CGGCCAGGGC GGGCTTGCGC CATGCGGCCC GAGAGTTTCG     600

GACGGCACCC GCCGCTTTCT GCTTAGCTTG TTAGCAGCCT TTTTCTGCGG CGAATCCGAA     660

ATCTTAAGTC AGGGAGCTGC CGCCGCTCGC CAGTGAGCAG AAATGCTTTC CGAAGCGCAA     720

GCCCGGCGGA GCAGGTTGTC TGCGCGGGGA GCAGAGAAGG CACCCTTTGG TTGGTGCTCT     780

GAGACGACCG GGAGGGACAG ACGGACTGGT GGCGTGTTAG GAGTGCATGG TGGCTTTGCG     840

TATTTAAGGG CGCAACACTT CAAACATAAC GAAGCTTAGT GGAGCGGGAT TTGCCGCCCT     900

CGCCACCAGA GAGACCTGGC TGGGGTTCTG TAAGATCGGT TGCGGTTCTT TGAGGTTCGG     960

AGTGGGTGAG ATGAACCACT GACCTCTTGG GATCGCGTCT GGAGAGTAGC TAGTATTCTT    1020

CGAGCTTCGG AAGCAAGAGG GAGAGCAAGC CTAGCAGAGG TACCCATTTC ATTTCCAGTT    1080

TGCTCGGTAG CTGGTGATTG GAAGACACTC TGCAACATTA CTCACTGAAG GCCTGAGACG    1140

CAGCCCCACC TCCCAGTTTC TTTACTAACT TGGGTCTGAC TTTTGTCAAA AGGCATCATG    1200
```

-continued

```
GCTGCCCTCC GGCCTCTGGT GAAGCCCAAG ATCGTCAAAA AGAGGACCAA GAAGTTCATC    1260

AGGCACCAGT CAGACCGATA TGTGAAAATT AAGGTATGTG GTTCTGGGGT GGGGGTTAAG    1320

ACCTGAGCAC ACATTTCTCG TTATCGCTTG TCTCTGCATT TTAAAAAGTT CGTTTTAAAG    1380

ATGACACTTT GTTTTATATT TATGCGTTCG AAGGGCAGGG TGAATCACTT TAAAGGAGTG    1440

GATTCTCTCC TTCCTGTCTT GTGGTGTCCA GGTCAGATTT AGTTTGTCTG ACAGCAGGCA    1500

CTTTGAAGTC ATCTCTGCAC CCTGACCCTG TATTTGAAAG ATCTTTGGGG TTTTGTCTGC    1560

ACACGCAGGC ACATGCATGC ATGGAATTGA ACCTCTGGAA GAGCAGCCAG TGCTCTTAAC    1620

TGCTAAGACC TCTCTCTGGG CCTGCAGATC ACCTGTTGGC TGGATGGGCA TGCACACCCA    1680

GCAGTTCAGC AGTTAACTGA TCCCTCCTCC CTACTTAATT GCAATGGAAG ATGATGTTGA    1740

AATTCCAGTG CAAGTGCTAG GGATGGAGCC CAGGGCCCTG TGCATGCCAG GCAGACACTG    1800

CTAACTGAGC TACACCTCGG CCTTTGGTGT GTGTTTTATG ACATGACCCC CTTGAATTCT    1860

GTCCCCTTCC TGCACACACA TACAAGAGCT GCCAGTTTGC ACAGAGACTA ACTTGCCTGT    1920

GTGTCTTCAG CGAAACTGGC GGAAACCCAG AGGCATTGAC AACAGGGTGC GGAGAAGGTT    1980

CAAGGGCCAG ATCCTGATGC CCAACATCGG TTATGGGAGC AACAAGAAAA CCAAGCACAT    2040

GCTGCCCAGC GGCTTCCGCA AGTTCCTGGT CCACAATGTC AAGGAGCTGG AGGTGCTGCT    2100

GATGTGCAAC AAGTGAGTTG GGCCCCTGGC TGGGAGTGTG CCTGCCTCCT GTGAGACTGA    2160

GGCCACTGCA GTGGGCATGC TTATGAGGAA AGAGGACGTG TTCCCTTGGT TGAAGCCTGA    2220

GACTGGAGAA GAAGGTCTTT TTACAGTGGG TGTTCAGTGT CCTTTATGGT CCTGTGTGGA    2280

ACACTGCTAT AGTGTCACGA GACTGCAGGG GCCTGTGTCT AACCTAGGAC CTAAGCTGTG    2340

CTTGGCTCTG CTCTGAACGG GTGGATTTGC AGAGCAGCTC AGGTCTTTTG GGGCTGAGGT    2400

AGAGAAAAAG TCTCCACGCA CAGCTGTAGA GAGAAGGTTG TGGGGTATTC TGGGTACTTT    2460

GAGCAAGTTA CAACCCTTGG TGACCTCTGA GATGCAAAAC CAAGGCCTCT CAGGAAATAC    2520

TCTTGACATT GGATATGAGG GTGTGATGGA AATAGTTTAT TTTTCCCAAG TAAACTAGGA    2580

CTGCAGAGAG TGTATGTGTT CGGGGTTATA AGGATTTGTT TTCTAAGGTG GTTGTCATGC    2640

AGATGGAGAG GAGTCCTATG GGGAGATTAT GTTGTGCATT TCACAAGGCC TTGAAGTGCT    2700

ACAAGTTCCC TTTGGAAGGA TGGATGCAGG AGAGAGAATG TGTGTTGTAC AGCAGCAGTC    2760

CATGAGGCAG TGTTGATGGT GCAGTGTTAT GGGCACTGCA TTTCTAATGG GTACATCTGC    2820

CCTAGGAATA GCTCTTGGCC TTGTCAGACC CTGCAGGTGC ACCGCTCACT GAGTTCTGTC    2880

TCTGGGCATT TTCCTCTGTA TCAGCTACCG AGCAGGGCAA GTTGCAGGGT AGTTACAGAA    2940

AAACCATTGG TTCCTGAGTG GTAAAGAGTC CTGGGTGGG ATATGGCAGC ATGTGACTTG    3000

TGAATGGTGA GTGTGCTAGA CAGCTATAAA TGCATGTGGC CCGGGATGGG TGCTTCCCGT    3060

TAGAACGTGA TGCACTCTGT CCCCAAATCT GTCAGGTGGT GTCTGTCTGT ATTAGGTATT    3120

TGCCATTTGT ATGCTTTCCA TAGCTCTGCC ATCCTGCTTC TCTAGGGGTT TTTCCTCAGC    3180

TCCCGGTCTA TGGCTTCACG GTCATCTCCA TGCTGGGAAT GTGTTCCCTT AGGACAGATT    3240

GTCAACACTT TGAGGGAACA CGGGCAGTGT TTGTTGTTCA CGCTGCTTGA ACTGTGTACC    3300

TTACAGTGGT TGCACTGGAA GCCTTTGGCT CCAGTTGGAA GAATTCTGGG TTACTCAGTG    3360

CGACGACGAA TTAAGCGATT TCCCTGGTGA CCTTTCTGGT TTGCTTCTCT TTCAGATCTT    3420

ACTGTGCTGA GATTGCTCAC AATGTGTCCT CTAAGAACCG AAAAGCCATT GTAGAAAGAG    3480

CAGCACAGCT GGCCATCAGA GTCACCAATC CCAACGCCAG GCTACGCAGC GAAGAAAATG    3540
```

-continued

```
AGTAGATGGC TTGTGTGCAT GTTTTATGTT TAAATAAAAT CACAAAACCT GCCGTCGTAT      3600

TTTCTATGTT TTTGGTAACT GGAGATTGTT CTTTGCTGCT TGTTCTGGGG GAGACAGCAG      3660

GGTTCAGAAT CCCATGCTAG TCTTGGTTGG CTGCAGGTGG AAGAGGGGAA AGGCCTTGAC      3720

CCTCTACAGT GTAGGTACAC TTAGAGTCTG GGGACC                                3756

(2) INFORMATION FOR SEQ ID NO:2:

(i) SEQUENCE CHARACTERISTICS:
        (A) LENGTH: 742 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

GGATCCGGAG ACGGTGGACG GTACCCCGCC GGCCCCCTGC TCCCGGGTGT GGCCGGGAAG        60

GGTGCACCTG GGCCTGAGGC GTGCCCATGT AGGGTCCCGG TCGTTGGACA AGACTTCGTT       120

TCCCACGCTC TCATTTCCCG CCCCCCGCCC TCGGAGTGTT TCCCTGTCGG TCGGTCGATC       180

GGTCGGGAGG TGGGGACCGG CCTGAGCTGG ATGGTGTGTC CTGGATTTTG GGGGAGCCAA       240

GTCCCCGTCT GGAGCTCCGG ACAGACCGAT ACCTGCCCGC GTGGGCAAGC CGGGAAGGGC       300

TTCCCGGCTG GCCGGCCGGC TCCACCTCCT TCATGTCCCT GTCCCTTCCC TGCGGTCACG       360

CTCCCCGGGT CGACCAGATG GCTCTGAGAG CGCTGGGTCT GGCGACTCTA GGGCAGGGCT       420

GGGGGACAAG TGTCCGGATG GGGGTTCCGG GGATACCCCC ACGTCCTGTG GGTGGGCCCC       480

GCTGCTGGGC ATGGACATTT TTCGCGGCCG AAATACGCCT TTTCTGTCAC CAGGTAGATG       540

CTGACACGAT CCTCTTCAGC GCCTGTCGCT GGAGACCTTG GGCCTCTGGA TGCACGTGGG       600

GGGCTTTGGG CTTTCGGCTG CTGTCCAAGG CCTGACCCTG CCCTTTGCAC CCCGCGTGGG       660

GCCGCTCGCC TGGGCCTGTG CGCCGGCTCT CACTTGTGCA TCCAGCTGGC CCGTGCTGCG       720

GTGTCTCCTC CGGTCTCTGG CT                                               742
```